United States Patent [19]
Sokal

[11] Patent Number: 5,826,594
[45] Date of Patent: Oct. 27, 1998

[54] FLOSS DISPENSER WITH MEMORY AID FOR FLOSSING UPPER AND LOWER TEETH IN SEPARATE SESSIONS AND METHOD

[76] Inventor: David C. Sokal, 209 E. Jackson St., Mebane, N.C. 27302

[21] Appl. No.: 783,765

[22] Filed: Jan. 15, 1997

Related U.S. Application Data

[60] Provisional application No. 60/010,425 Jan. 22, 1996.

[51] Int. Cl.[6] .................................................. A61C 15/00
[52] U.S. Cl. .......................... 132/200; 132/321; 434/263
[58] Field of Search ..................................... 132/321, 322, 132/200; 434/263; 225/17, 77

[56] References Cited

U.S. PATENT DOCUMENTS

| | | |
|---|---|---|
| D. 189,548 | 1/1961 | Gershen . |
| D. 256,999 | 9/1980 | Haagedoorn et al. . |
| D. 360,056 | 7/1995 | Tamez . |
| 2,929,541 | 3/1960 | Castelli et al. . |
| 3,126,129 | 3/1964 | Weinberg .................................. 434/263 |
| 3,227,127 | 1/1966 | Gayle . |
| 3,968,900 | 7/1976 | Stambuk . |
| 4,016,892 | 4/1977 | Chodorow . |
| 4,073,419 | 2/1978 | Tarrson et al. . |
| 4,127,190 | 11/1978 | Sunnen . |
| 4,807,752 | 2/1989 | Chodorow . |
| 4,844,104 | 7/1989 | Martin ...................................... 132/321 |
| 4,934,389 | 6/1990 | Pettiford . |
| 5,016,660 | 5/1991 | Boggs . |
| 5,076,423 | 12/1991 | Russack . |
| 5,184,959 | 2/1993 | Oryhon et al. ........................... 434/263 |
| 5,246,022 | 9/1993 | Israel et al. . |
| 5,282,563 | 2/1994 | Oliver et al. .............................. 225/77 |
| 5,299,723 | 4/1994 | Hempel . |
| 5,704,087 | 1/1998 | Strub ........................................ 434/263 |

FOREIGN PATENT DOCUMENTS 4305013 8/1994 Germany ................................ 433/229

OTHER PUBLICATIONS

"Toothbrushing Frequency as It Relates to Plaque Development and Gingival Health", Lang et al, *Journal of Periodontology*, 1973, 44: 396–405.

"Establishing and Maintaining Clinically Healthy Gingivae in Rhesus Monkeys", Caton, Journal of Clinical Periodontology 1979, 6: 260–263.

*Primary Examiner*—Todd E. Manahan
*Attorney, Agent, or Firm*—Richard S. Faust

[57] ABSTRACT

Personal oral hygiene of the general population is improved by making flossing considerably easier and less time consuming than it is when performed pursuant to current recommendations of the dental profession. This invention is an improved method for cleaning the interproximal tooth surfaces, comprising alternating the flossing of the lower teeth and the upper teeth in separate flossing sessions. A preferred embodiment is to floss the lower teeth on Mondays, Wednesdays and Fridays, and the upper teeth on Tuesdays, Thursdays, and Saturdays (or Sundays). This invention can maintain gingival health with less than half the time and effort of currently recommended methods. An alternative embodiment is to floss the lower and upper teeth on alternate days, irrespective of the day of the week. The invention may be carried out with any type of dental floss, and with any mechanical or electrical flossing aid, as well as other kinds of interdental cleaners. The invention includes novel floss dispensing devices to help users remember to floss properly according to the invention. One such device is a floss dispenser with six floss cutters (FIG. 1). A memory aid in the form of day-of-the-week indentifiers next to each cutter reminds the user which teeth to floss on which day.

22 Claims, 5 Drawing Sheets

FLOSS DISPENSER WITH MEMORY AID
FOR FLOSSING UPPER AND LOWER
TEETH IN SEPARATE SESSIONS AND
METHOD

CROSS REFERENCE TO RELATED APPLICATION

This application claims the benefit under Title 35, United States Code §119(e) of U.S. provisional application Ser. No. 60/010,425 filed Jan. 22, 1996.

BACKGROUND: TECHNICAL FIELD

This invention relates to personal oral hygiene, and, more particularly, to dental flossing.

BACKGROUND: PRIOR ART

Daily cleaning of interproximal tooth surfaces is recommended by the American Dental Association, along with a minimum of twice-daily brushing. Cleaning of the interproximal tooth surfaces is most commonly done by flossing one's teeth, but may also be done with interdental cleaners. Dental professionals agree that regular flossing prevents gingivitis by reducing the buildup of plaque on the interproximal surfaces of the teeth. Preventing gingivitis helps prevent the development of periodontitis. Periodontitis is a severe disease of the teeth and gums, and is the most common cause of tooth loss among adults.

Unfortunately, for many years it has been clear that most people do not floss regularly. While about 90% of adults brush their teeth on a daily basis, only a small percentage of adults floss their teeth on a daily basis. This has been known for many years, and is considered a major dental health problem. Over the years, many different approaches have been developed to remedy this situation, but none has been very successful.

Some of the problems that discourage people from flossing are:

a) Flossing is difficult and/or boring, and takes too long.
b) The floss breaks and/or strands of floss get stuck between two teeth.
c) Manual flossing can hurt a finger, due to the tightening of the floss during use.
d) Among people with arthritis, problems with decreasing strength and/or dexterity may make flossing more difficult.

Several different approaches have been taken to solve these problems, including: (1) mechanical flossing aids to make it easier to floss, (2) electrical flossing aids to make it easier to floss, and (3) devices to make it more convenient to carry or have access to dental floss. (1) Mechanical flossing aids Relatively few mechanical flossing aids have been marketed. Two of those which are presently on the market are Interdental Flossups (TM) and Gripper Floss (R) (U.S. Pat. Nos. 4,016,892 and 4,807,752, respectively). Both of these devices have serious problems.

The device of U.S. Pat. No. 4,016,892 has a very short length of floss, only about ¾ inch. For teeth that are tightly opposed, the floss may break, and a completely new device is needed. Without the ability to use a new section of floss between teeth, as recommended by the American Dental Association instructions, breaking floss is likely to occur frequently and lead to the use of several devices to floss one's teeth. Secondly, after being used on two or three teeth, the floss elongates and it is impossible to exert enough force to push it between the next interproximal space. Thus several devices may be needed to floss one's teeth. Of the problems noted above, this device only avoids discomfort to the fingers about which the floss would be wrapped.

The device of U.S. Pat. No. 4,807,752 consists of "dental floss segments with fingertips" or handles. The floss segment is longer than that of the '892 device; it is about three inches. The handles do make it easier to hold the floss. However, in order to prevent the floss from breaking, the floss has been made thicker than most brands of dental floss. This thicker floss is harder to get between tightly opposed teeth, and can thus be uncomfortable to use. Of the problems noted above, this device reduces finger discomfort and floss breaking, but has its own disadvantage, namely thicker floss.

(2) Electrical flossing aids

Electrical devices, such as described in U.S. Pat. No. 5,016,660, are generally cumbersome, awkward to use and expensive. They usually also have some of the same problems as cited above for mechanical devices.

(3) Convenience devices

A number of dispensers and containers have been devised to make it more convenient or appealing to carry or use dental floss. For example, the floss holder shown in U.S. Pat. No. D-360,056 dispenses floss through the mouth of a helmeted football player. U.S. Pat. No. 4,934,389 describes a floss dispenser that can be made as part of a tooth paste pump. U.S. Pat. No. 5,076,423 describes a credit-card-sized floss dispenser which is easier to carry in one's pocket or wallet. U.S. Pat. No. 5,246,022 describes a wall-mounted holder that can make it easier to keep dental floss dispensers easily accessible.

While all of the above devices help make flossing slightly easier or more convenient, none of them address all four of the barriers to flossing noted above. There is no data showing that they have had a measurable impact on improving flossing compliance among the general public. There continues to be a desperate need for a practical, inexpensive way to make it easier for people to floss their teeth regularly and thereby increase flossing compliance.

With respect to determining the frequency of flossing required for oral health, two studies from the 1970's are helpful.

In *Journal of Periodontology* 1973, 44: 396–405, Lang showed that for the prevention of gingivitis, careful, supervised cleaning of the teeth every other day was just as satisfactory as cleaning the teeth twice a day. However, dentists generally felt that while this was interesting from an experimental point of view that this would not be true for the average citizen. The reason is that in Lang's study, the subjects' oral hygiene was supervised by a dental hygienist. Lang described the supervision as follows:

"Using the Plak-Lite (TM) disclosing system, a dental hygienist ensured that no plaque remained following the performance of oral hygiene."

A "disclosing" system was used. A disclosing system includes a disclosing solution which is a special dental solution that is used to identify plaque on a person's teeth. In Lang's study, if the disclosing solution revealed any remaining plaque, the dental hygienist would presumably ask the person to brush or floss again. Unfortunately, the exact details of the remedial process were not specified in Lang's paper. He did not specify how any additional cleaning was done.

In *Journal of Clinical Periodontology* 1979, 6:260–263, Caton reported a study in Rhesus monkeys conducted to identify the "minimal frequency of plaque removal for the establishment and maintenance of clinically healthy gingivae." The monkeys all started with "gross amounts of plaque and moderate to severe gingivitis." Caton compared three methods of cleaning their teeth. Two involved the use of a chlorhexidine solution, and one was just the simple use of tooth brushing and dental floss. While cleaning teeth once or twice a week was not adequate, Caton showed that cleaning the monkeys' teeth three times a week was adequate: "All three methods of plaque removal, when done thrice weekly, gave similar low . . . gingival scores." Caton noted that plaque removal three times a week rather than daily would be advantageous for dental studies of non-human primates studies because it would lessen the frequency of sedation. Non-human primates have to be sedated before tooth brushing or flossing can be done. Fortunately, Caton was precise about his description of his method of verifying the plaque removal in these animals:

"Plaque removal was assessed by topical application of a disclosing solution. Any plaque so disclosed was removed with the toothbrush."

The details contained in this description are important. It should be noted that flossing was done only once. Any extra cleaning was done with a toothbrush. This means that flossing three times a week, combined with good tooth brushing, proved adequate for Rhesus monkeys. Caton, of course, was specifically interested in cleaning the animals' teeth three days a week in order to minimize the need for sedation. He did not report possible modifications of this strategy for humans.

SUMMARY OF THE INVENTION

This invention provides improved cleaning of the interproximal tooth surfaces, which is usually done by flossing, in such a way as to significantly increase flossing compliance among the general population, while making flossing considerably easier and less time consuming than it is when done pursuant to current professional recommendations. In one aspect, the invention comprises the cleaning of the interproximal tooth surfaces by alternating the flossing of the upper teeth and lower teeth in separate flossing sessions. In one preferred manner of practicing the invention, the lower teeth are flossed on Mondays, Wednesdays and Fridays, and the upper teeth on Tuesdays, Thursdays, and Saturdays or Sundays. Flossing carried out in accordance with this aspect of the invention is much easier than flossing all the teeth at the same time every day, and is adequate to maintain gingival health. In other aspects, the invention takes the form of novel designs for dental floss dispensers that incorporate a memory aid prompting the user to correctly alternate flossing sessions between the upper and lower teeth.

DRAWING FIGURES

DEFINITIONS lower teeth/upper teeth

Figure 1:
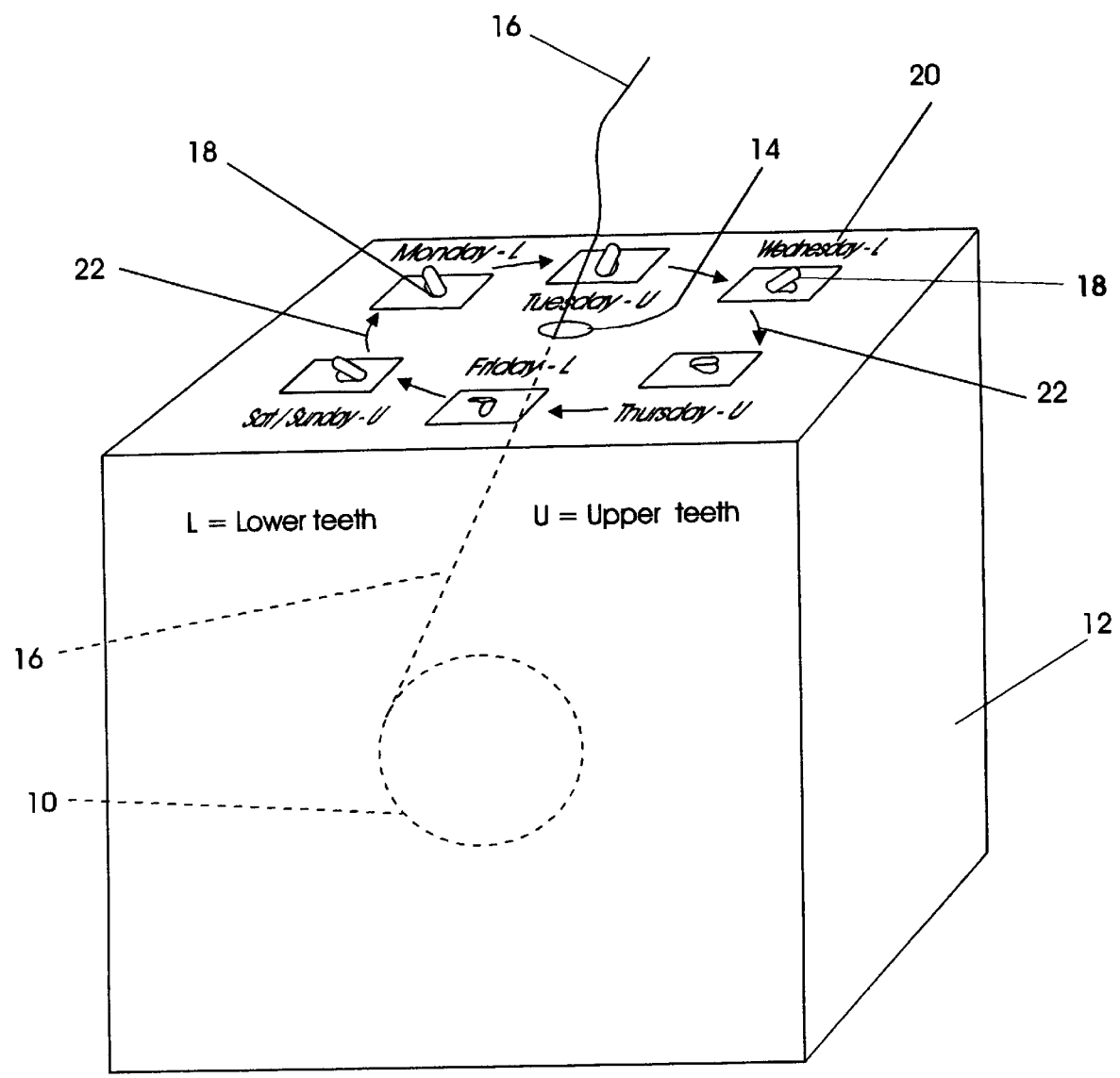
FIG. 1 shows a dental floss dispenser constructed in accordance with the present invention. The dispenser has six floss cutters and a memory aid to help people remember which teeth to floss on which days.

When the terms "lower teeth" and "upper teeth" are used herein, it should be understood that this means half of the teeth, i.e. at any time these terms could be substituted by the right or left half of the teeth.

fixed days/non-fixed days

The term "fixed days" refers to those situations where the lower teeth are always flossed on certain days of the week, with the upper teeth flossed on alternating days. "Non-fixed days" refers to flossing the lower teeth every other day, with the upper teeth flossed on alternating days so that flossing of lower/upper teeth may occur on different days in successive weeks.

flossing

The term "flossing" is used to denote cleaning of the interproximal tooth surfaces. While most people do this using dental floss, other means may also be used, such as those described in the prior art section of this specification. Thus, when the term "flossing" is used, the cleaning method is not necessarily restricted to the use of dental floss.

separate flossing sessions

The term "separate flosssing sessions" refers to temporal separation of the flossing of the lower teeth from flossing of the upper teeth, with the temporal separation being typically measured at least in hours, and usually by one day.

compliance

"Compliance" is used herein as a technical medical term which means the degree to which patients follow health care instructions. Numerous studies of compliance have shown that compliance gets better as the instructions are made simpler and the task is made easier and annoyances/ discomforts are reduced.

DETAILED DESCRIPTION OF THE INVENTION

It has been discovered that when one flosses all of one's teeth in one session, every day, as currently recommended by the dental profession, problems with flossing almost always occur during the second half of the flossing session. Thus, if one first flosses the upper teeth, followed immediately in the same session by flossing the lower teeth, problems such as breaking floss, floss sticking between teeth, finger discomfort and finger cuts occur predominantly while flossing the lower teeth. This insight led to a basic implementation of the invention, mainly, flossing the lower teeth on Monday, Wednesday and Friday, and flossing the upper teeth on alternating days, i.e., Tuesday, Thursday and Saturday or Sunday. Since the duration of flossing at each session was halved, the above identified flossing problems were greatly diminished. This method reduces the time and effort needed for flossing by nearly 60% compared to current recommendations of the dental profession. Current recommendations call for flossing the whole mouth seven times per week. With the method of the invention, the whole mouth is flossed three times a week, that is $3/7$ or reduction of $4/7$, or 57%, in the work required by the current recommendations. Thus, by greatly eliminating the flossing problems associated with broken floss, stuck floss and discomfort and reducing the time required by 57%, flossing has been made significantly easier and compliance has been improved.

FIG. 1 shows one preferred embodiment for a dental floss dispenser which helps users remember which teeth to floss. As in a typical dispenser of the prior art, a roll 10 of dental floss 16 is contained in a small rectangular enclosure 12: there is an opening 14 on one surface of the enclosure, from which a strand of floss 16 issues. According to this embodiment of the invention, six floss cutters 18, one for each flossing in a week, are located on the dispenser proximate to hole 14. A label 20 (e.g. Wednesday L) is positioned next to each cutter 18 to serve as a memory aid so that the user is prompted to floss the correct teeth each day. Arrows 22 facilitate proper movement from cutter to cutter.

Figure 2:
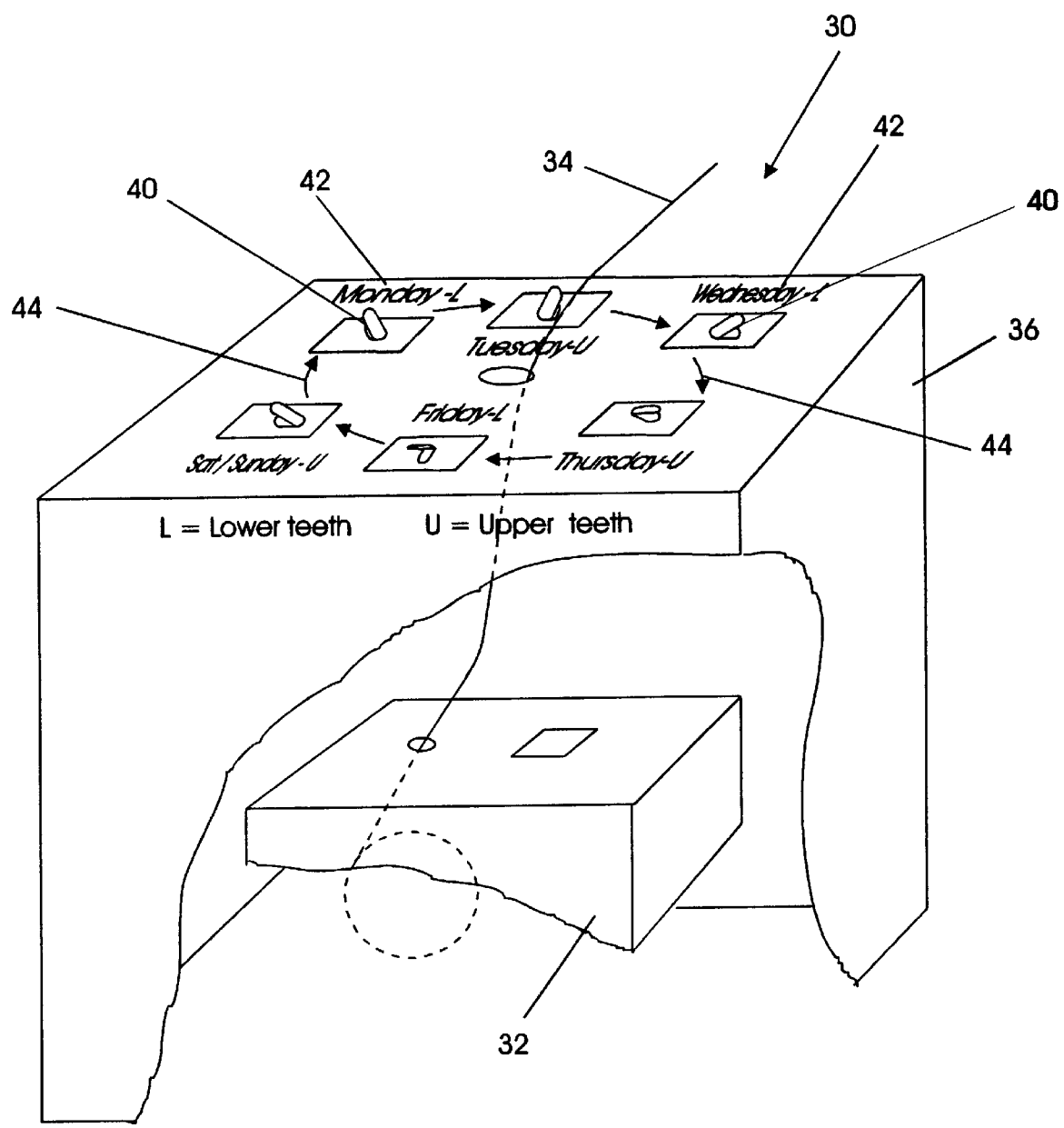
FIG. 2 is a partly cut away view of a two-part dental floss dispenser of the invention that includes a container holding a conventional floss dispenser.

FIG. 2 shows a first alternative embodiment wherein the dispenser 30 has a first dispenser portion in the form of a conventional floss dispenser 32 for paying out the user's favorite floss 34 and a second dispenser portion in the form of a container 36 that encloses and holds floss dispenser 32. Container 36 has an opening 38 on one surface through which a strand of floss 34 issues. Six floss cutters 40, labels 42 and arrows 44 similar to those shown in FIG. 1 are located around opening 38. Thus, the embodiment of FIG. 2 permits the present invention to be carried out with the conventional dental floss and dispenser of the user's choosing. It will be appreciated that the shape and size of container 36, and the means for holding the conventional floss dispenser therein, may be readily devised by those of skill in the art for accommodating a wide range of conventional floss dispensers and, therefore, further detail of the container structure is not deemed necessary.

Figure 3:
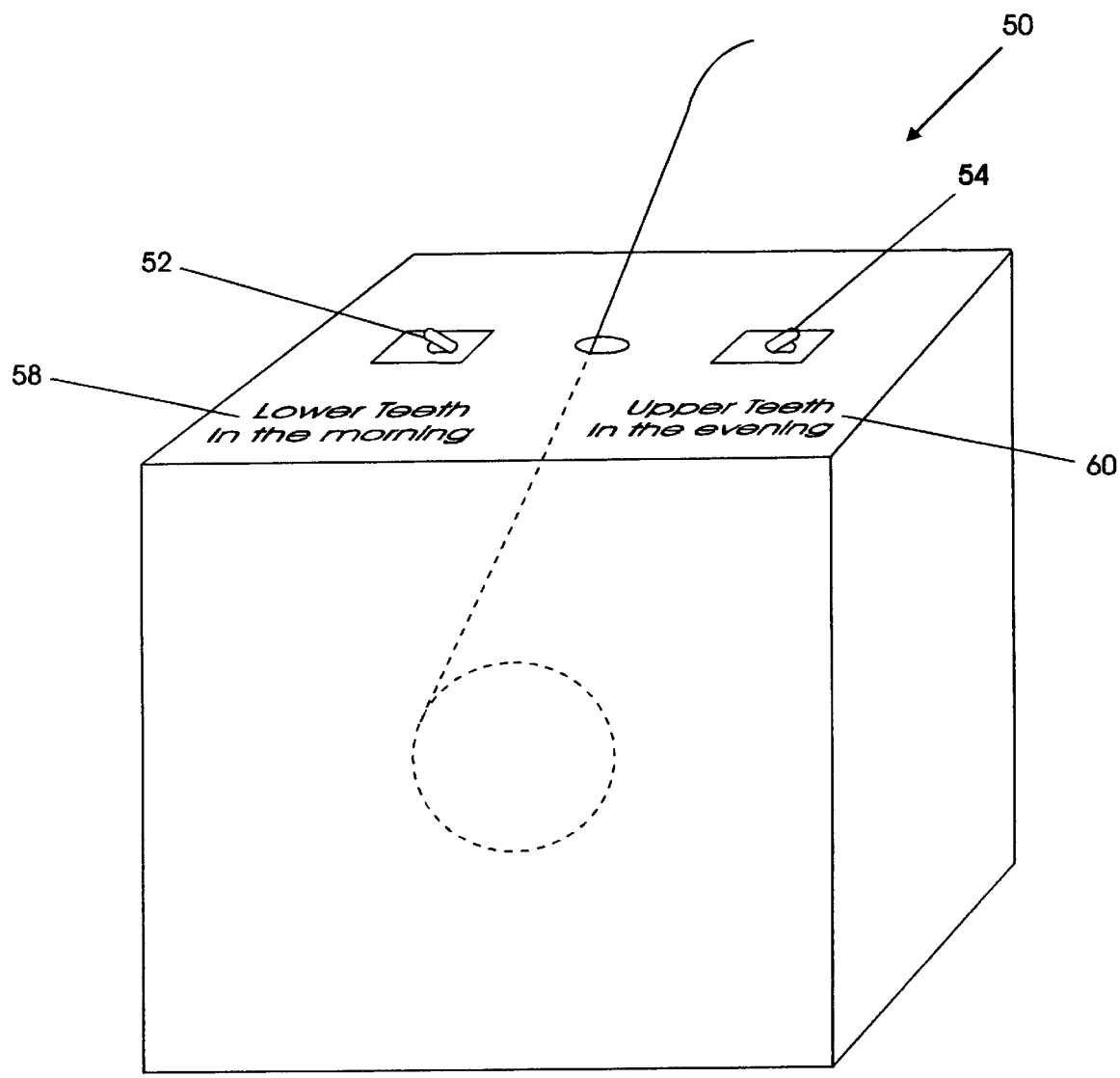
FIG. 3 shows a floss dispenser with two floss cutters and twice-a-day instructions.

FIG. 3 shows a floss dispenser 50 with two floss cutters 52, 54 and labels 58, 60. For people who simply wish to floss all their teeth each day, or people who have serious pre-existing periodontal disease warranting daily flossing, this device reminds them which teeth to floss in the morning, and which to floss in the evening.

Figure 4:
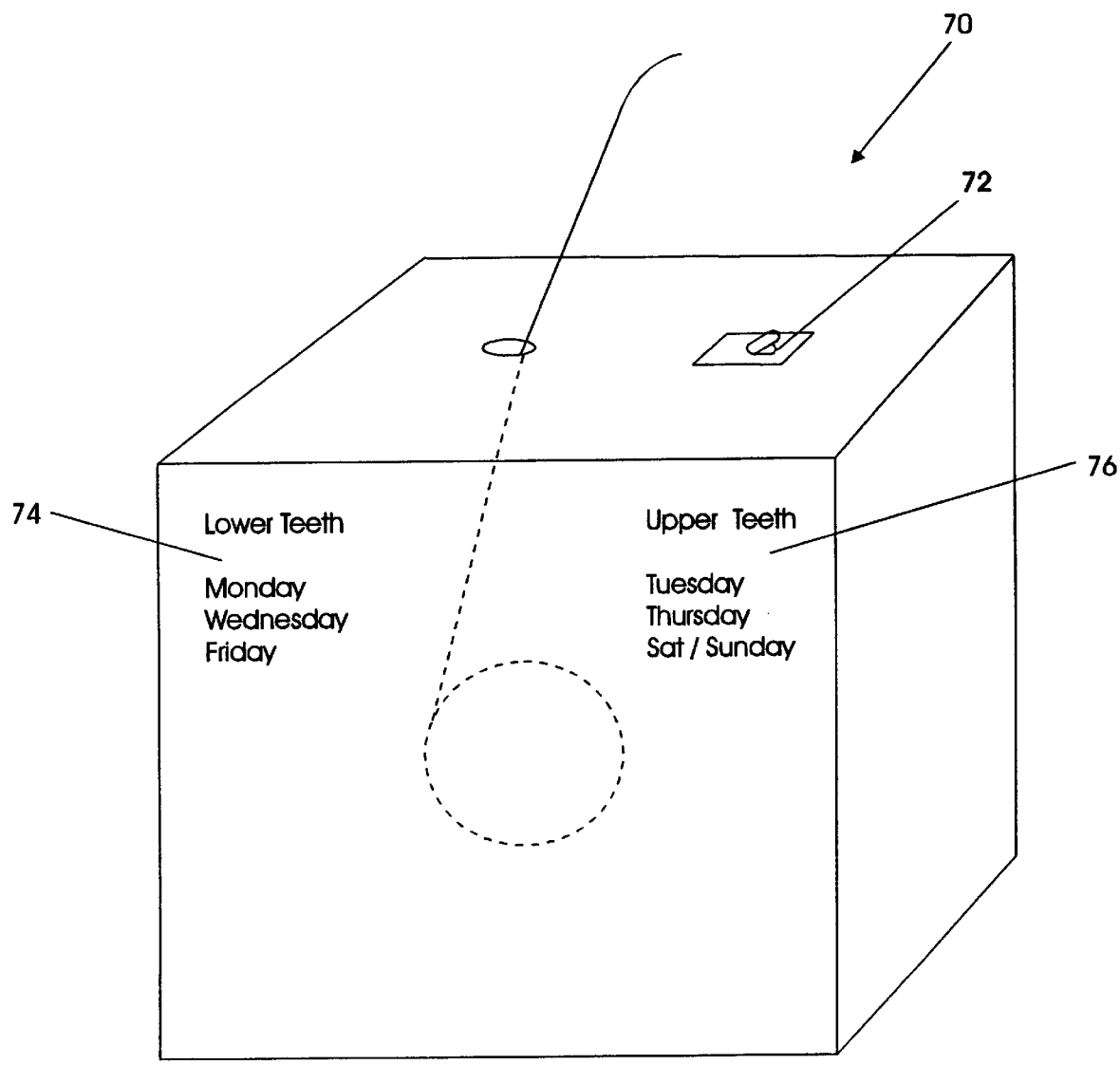
FIG. 4 shows a floss dispenser with one floss cutter and six-times-a-week instructions.

FIG. 4 shows a floss dispenser 70 with one floss cutter 72 and special labeling 74, 76 reminding the user which teeth to floss on which days of the week.

Figure 5:
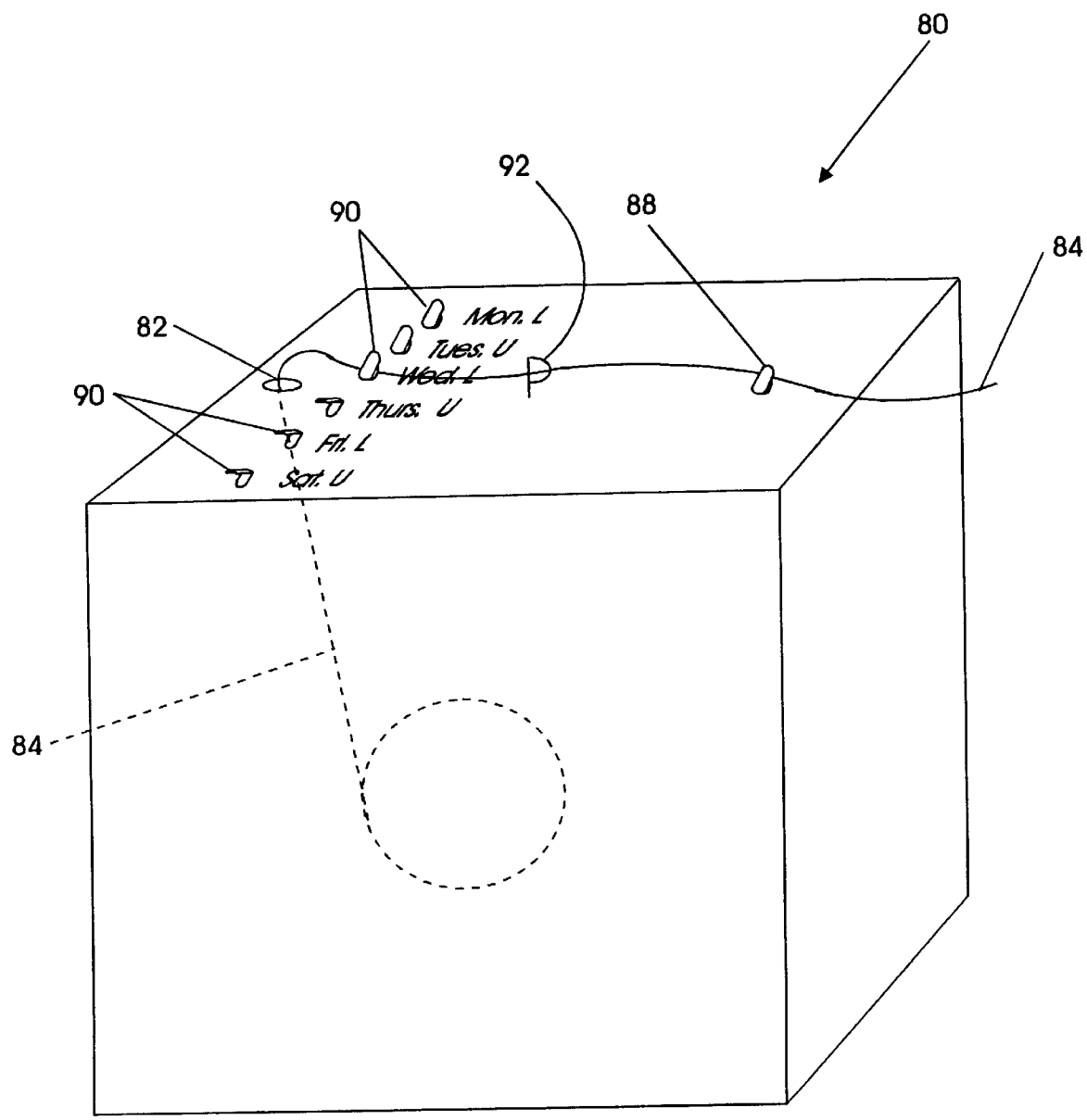
FIG. 5 shows a floss dispenser with a floss clip associated with each of the day-of-the-week labels.

FIG. 5 shows a dispenser 80 having a single opening 82 from which a strand of floss 84 issues and a single floss cutter 88. Between opening 82 and cutter 88 are six floss clips 90 and a guide hook 92. Dispenser 80 includes a memory aid comprising a day-of-the-week label (e.g. "Wednesday L") next to each clip 90. In operation, floss goes from opening 82 to the appropriate day-of-the-week clip 90, through the guide hook 92 and then to floss cutter 88. Clips 90 may be formed as simple plastic projections that resemble a floss cutter, but without any sharp edges. The clips serve to hold the floss by friction engagement and, in conjunction with the adjacent label, remind the user of the appropriate teeth to be flossed. Guide hook 92 serves to guide the floss to cutter 88 at an effective angle for cutting. As an alternative to the configuration of FIG. 5, a dispenser may be provided with multiple floss cutters with a clip next to each cutter in order to help avoid the floss slipping loose from the cutter, and in a sense "forgetting" which flossing was done last.

It should be noted that most floss dispensers have a cover that snaps open or closed, and fits over the top of the floss dispenser. The novel floss dispensers described herein may also have covers, but covers have been omitted from the above figures in order to better illustrate the key features of the invention.

Other Alternative Embodiments

A. Rotating ring reminder (fixed timing) :Instead of having a dispenser with six floss cutters, a dispenser of the invention may include a labeled rotating ring or disk with six click stops and an arrow or other indicator means. Each click stop corresponds to one of the six flossing times during the week. Labels on the disk or ring may be identical or similar to the labels in FIG. 1 and 2.

B. Electrical reminder means: Various electrical means may be assembled to remind the user which half of the mouth to floss on a given day. Such means may include a timer and/or a sensor and/or a liquid crystal display panel to display a message to the user about which teeth to floss on which day.

C. Memory Aid for every other day method: In the embodiment of FIG. 3, by removing the words "in the morning" and "in the evening" from the label, the dual-cutter floss dispenser may be used to remind the user which half of the mouth he flossed last. The label indicates that whenever a person flosses their lower teeth, he or she should use the cutter on the left side, near the label "Lower teeth." The next time the person comes to floss their teeth, they can see that the end of the strand of floss is caught under the cutter labeled "Lower teeth." They will therefore know that on this occasion, they need to floss their upper teeth.

Summary, Ramifications, and Scope

In summary, according to a preferred manner of carrying out the invention, a person cleans all of his or her interproximal tooth surfaces three times a week. This work is divided into six flossing sessions. Only one half of the teeth are flossed during each of the six flossing sessions. This invention makes it much easier for people to floss their teeth and, therefore, increases compliance.

This invention may be used in conjunction with conventional floss held by the fingers or with any other type of mechanical or electrical flossing aid or with other types of interdental cleaners. Although the description above contains many specificities, these should not be construed as limiting the scope of the invention, but as merely providing illustrations of some of the presently preferred embodiments of this invention. For example, those skilled in the art may devise many different types of textual, pictorial, mechanical and/or electrical memory aids to help people remember which teeth to floss on a given day. Thus the scope of the invention should be determined by the appended claims and their legal equivalents, rather than by the examples given.

That which is claimed is:

1. A method for flossing a person's teeth in an ongoing program of oral hygiene suitable for the general population comprising alternating the flossing of the upper teeth and the lower teeth in separate flossing sessions.

2. The method of claim 1 including the steps of flossing the lower teeth on the same three days each week and flossing the upper teeth on three other alternating days of the week.

3. The method of claim 1 comprising the steps of flossing the lower teeth on a first day, the upper teeth on the second day, the lower teeth on the third day, followed by continuing flossing of different halves of the teeth on alternate days.

4. The method of claim 1 wherein the flossing of the lower teeth is done in the morning and the upper teeth is done in the evening.

5. The method of claim 1 wherein the flossing of the upper teeth is done in the morning and the lower teeth is done in the evening.

6. The method of claim 1 including the step of dispensing the floss used in the flossing sessions from a dispenser having a memory aid prompting one to correctly alternate flossing sessions between the upper teeth and the lower teeth.

7. The method of claim 1 including the step of dispensing the floss used in the flossing sessions from a dispenser having multiple floss cutters labeled to prompt one to correctly alternate flossing sessions between the upper teeth and the lower teeth.

8. The method of claim 1 including the step of dispensing the floss used in the flossing sessions from a dispenser having indicia thereon indicating the fixed days of the week for flossing the upper teeth and the fixed days of the week for flossing the lower teeth.

9. The method of claim 1 including the step of utilizing a visible memory aid that prompts one to correctly alternate flossing sessions between the upper teeth and the lower teeth.

10. A dental floss dispenser having an associated memory aid comprising multiple floss cutters labeled to prompt a user to correctly alternate flossing sessions between the upper teeth and the lower teeth.

11. The dispenser of claim 10 including six floss cutters labeled to prompt a user to floss the lower teeth on the same three days each week and the upper teeth on three other alternating days of the week.

12. A dental floss dispenser having an associated memory aid that instructs a user to floss the upper teeth and the lower teeth in separate flossing sessions on alternate days.

13. A dental floss dispenser having an associated memory aid that instructs a user to floss the upper teeth and the lower teeth in separate flossing sessions on the same day.

14. A dental floss dispenser having an associated memory aid prompting a user to floss the upper teeth and lower teeth in separate flossing sessions.

15. The dispenser of claim 14 wherein said memory aid comprises indicia instructing a user as to which days of the week to floss the upper teeth and which days of the week to floss the lower teeth.

16. The dispenser of claim 14 including a first dispenser portion containing a supply of floss and a second dispenser portion incorporating said memory aid.

17. The dispenser of claim 16 wherein said second dispenser portion is a container that holds the first dispenser portion.

18. The dispenser of claim 17 wherein said second dispenser portion includes (i) an opening from which the floss from the first dispenser portion issues and (ii) at least one floss cutter.

19. A container for holding a conventional dispenser of dental floss so that the floss may be used in an ongoing program of oral hygiene wherein a user alternates flossing of the upper teeth and the lower teeth in separate flossing sessions, said container including means for issuing floss from the conventional dispenser and a memory aid prompting a user to floss the upper teeth and the lower teeth in separate flossing sessions.

20. The container of claim 19 wherein said means for issuing floss comprises a hole in the container.

21. A method for flossing a person's teeth in an ongoing program of oral hygiene suitable for the general population comprising alternating the flossing of a first half of the teeth with the other half of the teeth in separate flossing sessions.

22. A dental floss dispenser having an associated memory aid prompting a user to floss a first half of the teeth and the other half of the teeth in separate flossing sessions.

\* \* \* \* \*